United States Patent
Roy et al.

(10) Patent No.: US 11,576,746 B2
(45) Date of Patent: Feb. 14, 2023

(54) LIGHT AND SHADOW GUIDED NEEDLE POSITIONING SYSTEM AND METHOD

(71) Applicant: Kornerstone Devices Pvt. Ltd., Chennai (IN)

(72) Inventors: Santosham Roy, Chennai (IN); Cherukandath Rajendran, Coimbatore (IN)

(73) Assignee: Kornerstone Devices Pvt. Ltd., Chennai (IN)

(*) Notice: Subject to any disclaimer, the term of this patent is extended or adjusted under 35 U.S.C. 154(b) by 1001 days.

(21) Appl. No.: 16/334,693

(22) PCT Filed: Sep. 19, 2017

(86) PCT No.: PCT/IN2017/050410
§ 371 (c)(1),
(2) Date: Mar. 19, 2019

(87) PCT Pub. No.: WO2018/055637
PCT Pub. Date: Mar. 29, 2018

(65) Prior Publication Data
US 2021/0290335 A1    Sep. 23, 2021

(30) Foreign Application Priority Data
Sep. 20, 2016 (IN) .............................. 201641032007

(51) Int. Cl.
*A61B 90/13* (2016.01)
*A61B 34/10* (2016.01)

(52) U.S. Cl.
CPC .............. *A61B 90/13* (2016.02); *A61B 34/10* (2016.02); *A61B 2034/107* (2016.02)

(58) Field of Classification Search
CPC ... A61B 90/13; A61B 34/10; A61B 2034/107; A61B 34/00; A61B 2090/365; A61B 90/11; A61B 6/032
See application file for complete search history.

(56) References Cited

U.S. PATENT DOCUMENTS 4,296,329 A * 10/1981 Mirabella .............. A61B 6/583
250/252.1
8,401,620 B2    3/2013 Velusamy et al.
(Continued)

FOREIGN PATENT DOCUMENTS

| CN | 103300921 B | 3/2017 |
|---|---|---|
| EP | 1 887 960 B1 | 2/2008 |
| JP | 2017-512523 A | 5/2017 |

OTHER PUBLICATIONS

International Search Report dated Nov. 17, 2017, issued in connection with International Patent Application No. PCT/IN2017/050410, 3 pages.
(Continued)

*Primary Examiner* — Phong X Nguyen
(74) *Attorney, Agent, or Firm* — McDonnell Boehnen Hulbert & Berghoff LLP

(57) ABSTRACT

The embodiments of the present invention provide a system and method for light and shadow guided needle positioning. DICOM images of a patient are captured for identifying a point of insertion of a needle on the patient's body and a target point inside the patient's body. Needle coordinates are computed based on the captured DICOM images to position the mechanical arms. Light is projected at a particular angle on the needle to form shadows of the needle. Laser light beams are projected to form cross hair at the point of insertion. Images or videos of the point of insertion, shadow of the needle and the cross hair are captured and displayed on a monitoring unit. A virtual circle is projected on the
(Continued)

displayed image and is aligned with the point of insertion, shadow of the needle and cross hair in order to insert the needle precisely.

9 Claims, 8 Drawing Sheets

(56) References Cited

U.S. PATENT DOCUMENTS

| | | | | |
|---|---|---|---|---|
| 9,056,020 | B1* | 6/2015 | Termanini | A61F 2/4609 |
| 9,547,940 | B1* | 1/2017 | Sun | A61B 1/044 |
| 2003/0216750 | A1 | 11/2003 | Wong | |
| 2008/0091101 | A1* | 4/2008 | Velusamy | A61B 6/032 |
| | | | | 600/427 |
| 2008/0194945 | A1* | 8/2008 | Kukuk | A61B 6/463 |
| | | | | 600/424 |
| 2011/0092811 | A1* | 4/2011 | Yasui | A61M 5/52 |
| | | | | 382/128 |
| 2013/0218003 | A1 | 8/2013 | Rothgang et al. | |
| 2013/0218024 | A1* | 8/2013 | Boctor | A61B 46/00 |
| | | | | 600/476 |
| 2013/0245427 | A1 | 9/2013 | Rothgang | |
| 2015/0148668 | A1* | 5/2015 | Stolka | A61M 5/46 |
| | | | | 600/424 |
| 2015/0272700 | A1 | 10/2015 | Masuda et al. | |
| 2016/0015467 | A1* | 1/2016 | Vayser | G02B 1/048 |
| | | | | 600/245 |
| 2016/0113728 | A1* | 4/2016 | Piron | A61B 34/30 |
| | | | | 606/130 |
| 2016/0209203 | A1 | 7/2016 | Baur et al. | |
| 2016/0361128 | A1* | 12/2016 | Seeber | A61B 34/30 |
| 2017/0071672 | A1 | 3/2017 | Shochat | |
| 2021/0007808 | A1* | 1/2021 | Montague | G06T 7/12 |
| 2021/0290335 | A1* | 9/2021 | Roy | A61B 90/13 |

OTHER PUBLICATIONS

Written Opinion dated Nov. 17, 2017, issued in connection with International Patent Application No. PCT/IN2017/050410, 4 pages.
Indian Government, IP India, First Examination Report dated Aug. 1, 2018, issued in connection with Indian Patent Application No. 201641032007, 6 pages.
Indian Government, IP India, Hearing Notice dated Nov. 2, 2018, issued in connection with Indian Patent Application No. 201641032007, 3 pages.

* cited by examiner

LIGHT AND SHADOW GUIDED NEEDLE POSITIONING SYSTEM AND METHOD

The present application is a US national phase under 35 U.S.C. § 371 of international application PCT/IN2017/050410, filed Sep. 19, 2017, which claims priority to Indian Patent Application No. 201641032007, filed Sep. 20, 2016, which are incorporated herein by reference in their entirety.

TECHNICAL FIELD

The present invention is generally related to interventional medicine. The present invention is particularly related to needle positioning systems and methods for conducting medical procedure. The present invention is more particularly related to a system and method for guiding and positioning the needle towards a target point from a point of insertion on patient's body using shadows of the needle and light.

BACKGROUND OF THE INVENTION

In the field of interventional medicine, a medical procedure is performed for diagnostic or treatment purposes by taking a sample from a patient's body. For example, a sample tissue of a specific internal organ from the patient's body is collected by inserting a medical device such as a needle. As an insertion of the needle at correct angle and to a right depth is critical, the needle needs to be guided into a desired location within the body using various imaging and positioning techniques. These positioning techniques are typically used for purpose of biopsy, fluid drainage, catheter placement biopsy, amniocentesis, precision injections, cell aspiration, tumor ablation and the like. The advent of cross-sectional imaging techniques such as computed tomography (CT), magnetic resonance imaging, fluoroscopy and ultrasound, etc., have given rise to the use of image-guided interventions.

A common issue in conducting the core biopsies is in the identification of an exact location of a lesion and thereafter the accurate guiding of the biopsy needle to that lesion. Several methods and apparatus have been developed for core biopsies in connection with mammography and ultrasound. For example, a rigid frame-based system is used for collecting the sample from the brain.

The frame-based system requires an attachment of a frame to the skull of a patient to assist the surgeon in locating and collecting the sample from a targeted location within the brain. The frame is typically attached to the patient in an invasive manner. Such methods and apparatus still pose several issues and do not solve the problems entirely. For example, many such solutions are invasive and cause discomfort to the patient. Similarly, the accuracy of insertion is human based or dependent on individual skill set and requires a deep learning and heavy expertise in the field.

A common drawback of the existing systems is the need for multiple X-ray images of the lesion, thereby exposing the tissue to hazardous levels of radiation. These systems also do not provide a real-time imaging of the needle trajectory as the needle is inserted into the body. Most of the times, as the biopsy needle is secured in a fixed device and these systems do not provide a freedom of movement for the needle relative to the target tissue. Consequently, several needle insertions and manipulations are required for precise placement of the needle on the target point.

Thus, the conventional systems and methods for collection of a biopsy sample are complicated, cumbersome, and overlay invasively to the patient. Further, the use of such equipment is expensive, time consuming, and unjustified in small practices.

Hence, there is a need for a system and a method for accurately positioning the needle towards a point of insertion on a patient body without making any direct contact with the patient body. There is also a need for a needle positioning system and method that requires only one time calibration even for repeated usage. Further, there is a need for a system and method that promptly identifies any erroneous tilting of a needle.

Yet there is a need for a system and method for assisting the doctor or medical personnel while inserting the needle at precise location and at precise angle when performing the medical procedure such as biopsy procedure and other procedures which require the insertion of needle at the patient body. Yet there is a need for a system and method for positioning a needle using a camera. Yet there is a need for a system and method for positioning the needle using the shadows.

The above mentioned shortcomings, disadvantages and problems are addressed herein and which will be understood by reading and studying the following specification.

OBJECT OF THE INVENTION

The primary object of the present invention is to provide a system and method for a assistance in positioning a needle in interventional medicine using light and shadow.

Another object of the present invention is to provide a system and method for accurately positioning a needle towards a target point from a point of insertion on a patient's body without making any direct contact with the patient's body.

Yet another object of the present invention is to provide a system and method for promptly identifying an erroneous tilting of a needle through a continuous monitoring of the shadows of the needle.

Yet another object of the present invention is to provide a system and method receiving and displaying a plurality of Digital Imaging and Communications in Medicine (DICOM) images of a patient and allow clinician to select a point of insertion of a needle on the patient's body and a target point inside the patient's body.

Yet another object of the present invention is to provide a system and method for computing the needle coordinates to guide the needle based on the captured DICOM images to reach the target point.

Yet another object of the present invention is to provide a system and method for continuously capturing and displaying images or video of the point of insertion for real-time monitoring of needle/instrument insertion.

Yet another object of the present invention is to provide a system and method for aligning the intersection of cross-hairs in the projected image with the shadows of the needle and point of insertion in order to facilitate precise insertion of the needle.

Yet another object of the present invention is to provide a system and method for assisting the doctor in performing the medical procedures which require insertion of needle/instrument to the patient body for example biopsy procedure.

Yet another object of the present invention is to provide a system and method for calculating the Orbital-Angle and Crano-Caudal angle required for inserting the needle at the entry point marked on the image and calculating the length of the needle to be inserted into the patient body to reach the target point marked on the image.

Yet another object of the present invention is to provide a system and method for assisting the needle positioning method using the shadows of the needle created by the lights attached to the camera cross-hair attached to the positioning device.

Yet another object of the present invention is to provide a system and method for calculating the angle of insertion of the needle into the patient body, by receiving the images from imaging device to the system of present invention for selecting the entry points and the target points, for calculating the orbital, cranial/caudal angulation(s), and for calculating the length of the needle to be inserted into the patient body to reach the target point from the entry.

Yet another object of the present invention is to provide a positioning device mounted on a rail perpendicular to the patient table, which receives the calculated positions from the application and positions itself for the required angulation(s).

Yet another object of the present invention is to provide a system and method for assistance for needle placement used for medical procedure such as biopsy, liquid aspiration, multiple-needle insertion, targeted tumor ablation, etc.

Yet another object of the present invention is to provide a system and method for positioning a needle used in conjunction with a CT machine, MRI, fluoroscopy or Ultrasound and other imaging devices.

Yet another object of the present invention is to provide a system and method for continuous monitoring of a patient movement during the procedure and to for corrections in case of any such movements.

Yet another object of the present invention is to provide a system and method for positioning and inserting a needle without holding the needle with any device.

Yet another object of the present invention is to provide a system and method for positioning and inserting a needle by providing a full control of the needle to a radiologist.

Yet another object of the present invention is to provide a system and method in which there is no contact to the patient body and the device is separated well away from the patient thereby eliminating a need of ETO sterilization.

Yet another object of the present invention is to provide a system and method in which the complete needle body is monitored via shadows and precise insertion is achieved even with fine needles and further a needle erroneous tilting is easily identified by the shadow.

Yet another object of the present invention is to provide a system and method to suggest a virtual needle path on the DICOM images before actual insertion as a precautionary safety measure Yet another object of the present invention is to provide a system and method to monitor and detects patient while positioning the needle towards a target point from a point of insertion and compensates the movement by adjusting the position of patient's body.

Yet another object of the present invention is to provide a system and method to monitor an excursion point of entry of the needle and aid the clinician in order to maintain the consistent breath-hold or consistent phase of respiration of the patient at the time of positioning the needle.

These and other objects and advantages of the present invention will become readily apparent from the following detailed description taken in conjunction with the accompanying drawings.

SUMMARY OF THE INVENTION

The following details present a simplified summary of the embodiments herein to provide a basic understanding of the several aspects of the embodiments herein. This summary is not an extensive overview of the embodiments herein. It is not intended to identify key/critical elements of the embodiments herein or to delineate the scope of the embodiments herein. Its sole purpose is to present the concepts of the embodiments herein in a simplified form as a prelude to the more detailed description that is presented later.

The objects and advantages of the present invention will become readily apparent from the following detailed description taken in conjunction with the accompanying drawings.

The various embodiments of the present invention provide a system for positioning a needle based on light and shadow. The system comprises a planning station that receives and displays Digital Imaging and Communications in Medicine (DICOM) images of a patient from imaging device for a clinician in order to select a point of insertion of a needle on the patient's body and a target point inside the patient's body. A computing device is adapted for computing the needle coordinates based on the captured images and identified point of insertion and target point. The needle coordinates comprise two angles of insertion and insertion length of the needle to reach the target point. The computed angles are an orbital angle and a crano-caudal angle. A positioning device is configured for positioning one or more mechanical arms based on the computed needle coordinates. The positioning device is configured to move in horizontal direction on X axis, vertical direction on Y axis and the one or more mechanical arms are adapted to move in orbital angle on A axis and crano-caudal angle on Z axis. The computing device is also configured to display a virtual needle path based on the DICOM images before actual insertion as a precautionary safety measure. A light assembly is provided in the positioning device and is configured for projecting light at a particular angle on the needle placed at the point of insertion to form shadows of the needle using one or more LED lights. The light assembly further includes a laser light beam that project a cross hair at the point of insertion. An image capturing module is provided in the positioning device and is configured for continuously capturing images or video of the point of insertion, shadow of the needle and the cross hair. A centre of the image capturing module is aligned with the point of insertion marked on the patient's body. A monitoring unit is configured for displaying images or video captured using image capturing module. The monitoring unit is configured for projecting a virtual circle on the displayed images or video and for monitoring the alignment of the virtual circle with the point of insertion, shadow of the needle and the cross hair in order to facilitate precise insertion of the needle.

According to one embodiment of the present invention, the positioning device comprises an electronic control unit configured to receive the needle coordinates from the computing device and transform the needle coordinates into orbital and crano-caudal movement of the one or more mechanical arms in the positioning device.

According to one embodiment of the present invention, the electronic control unit comprises a controller configured for processing the received needle coordinates to generate corresponding electric signal. The electronic unit also comprises an electromechanical device. The electromechanical device is configured to move the one or more mechanical arms in horizontal direction on X axis, vertical direction on Y axis, orbital angle on A-axis and crano-caudal angle on Z axis based on the electric control signal/command received from the controller. The electronic control unit further comprises a feedback module configured for monitoring the movement of the one or more mechanical arms in X axis, Y axis, A-axis and Z axis for deviation from the computed needle coordinates. The feedback module is configured for providing a feedback to the controller about the deviations for enabling corrective action.

According to one embodiment of the present invention, the LED lights within the light assembly are configured based on one or more parameters such as a number of lights, angle of light, tilt angle and light intensity to generate different shadow patterns and shadow lengths of the needle.

According to one embodiment of the present invention, the laser lights within the light assembly are configured based on one or more parameters such as a number of beams, angle of beam, tilt angle and beam intensity to generate different cross hair patterns at the point of insertion.

According to one embodiment of the present invention, a method is provided for precise positioning of a needle using a light and shadow. The method involves receiving and displaying plurality of DICOM images, selecting a point of insertion of the needle on the patient's body and a target point inside the patient's body, computing needle coordinates and assist in aligning the needle using combination of shadow of the needle and laser cross-hair.

According to one embodiment of the present invention, the method comprising the steps of receiving and displaying plurality of DICOM images of a patient for selecting a point of insertion of a needle on the patient's body and a target point inside the patient's body. The needle coordinates are calculated based on the captured images. The needle coordinates comprise two angles of insertion and length of the needle insertion to reach the target point. The computed angle is an orbital angle and a crano-caudal angle. One or more mechanical arms are positioned based on the computed needle coordinates. The positioning device is configured to move in horizontal direction on X axis, vertical direction on Y axis and the one or more mechanical arms are configured to move in orbital angle on A-axis and crano-caudal angle on Z axis. An illuminating light beam is projected at a particular angle on the needle placed at the point of insertion to form shadows of the needle using one or more LED lights. A laser light beam is projected to form a cross hair at the point of insertion. The images or a video of the point of insertion, shadows of the needle and the cross hair are continuously captured using an image capturing module. A centre or focus of the image capturing module is aligned with the point of insertion marked on the patient's body. The images or video captured using image capturing module is displayed on a monitoring unit. The monitoring unit is configured for projecting a virtual circle on the displayed images or video and for monitoring the alignment of the virtual circle with the point of insertion, shadow of the needle and the cross hair in order to facilitate a precise insertion of the needle.

According to one embodiment herein, scanogram and axial section of the patient is taken and the point of insertion and the target point inside the patient's body is marked using CT console/table by the clinician manually. The point of insertion is measured from patient midline on the image and is marked with radio opaque fiducially. The DICOM images of the point of insertion are taken and forwarded to the computing device. The point of insertion and target point are registered on the computing device. Further, the computing system is configured to calculate the needle coordinates. The needle coordinates are then passed on to the positioning device to tilt the one or more mechanical arms by adjusting the movement A axis and Z axis, when needed. The centre of the image capturing module is aligned to the point of insertion to see the real time feed from the image capturing module. The one or more LED lights and laser lights are placed right angle to each other to form shadows of the needle and cross hair. Additional reference points are drawn on patient's body to detect any patient movement. A virtual circle is projected on the monitoring unit. The shadows of the needle, cross hair and virtual circle are aligned with the point of insertion. The stopper is marked at the needle based on the length of insertion computed at the computing device. Finally, needle is inserted through the point of insertion till the stopper marked at the needle in order to reach target location and by aligning the shadows with the laser cross-hair.

These and other aspects of the present invention will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the present invention without departing from the spirit thereof, and the embodiments include all such modifications.

BRIEF DESCRIPTION OF THE DRAWINGS

The other objects, features and advantages will occur to those skilled in the art from the following description of the preferred embodiment and the accompanying drawings in which.

Figure 1:
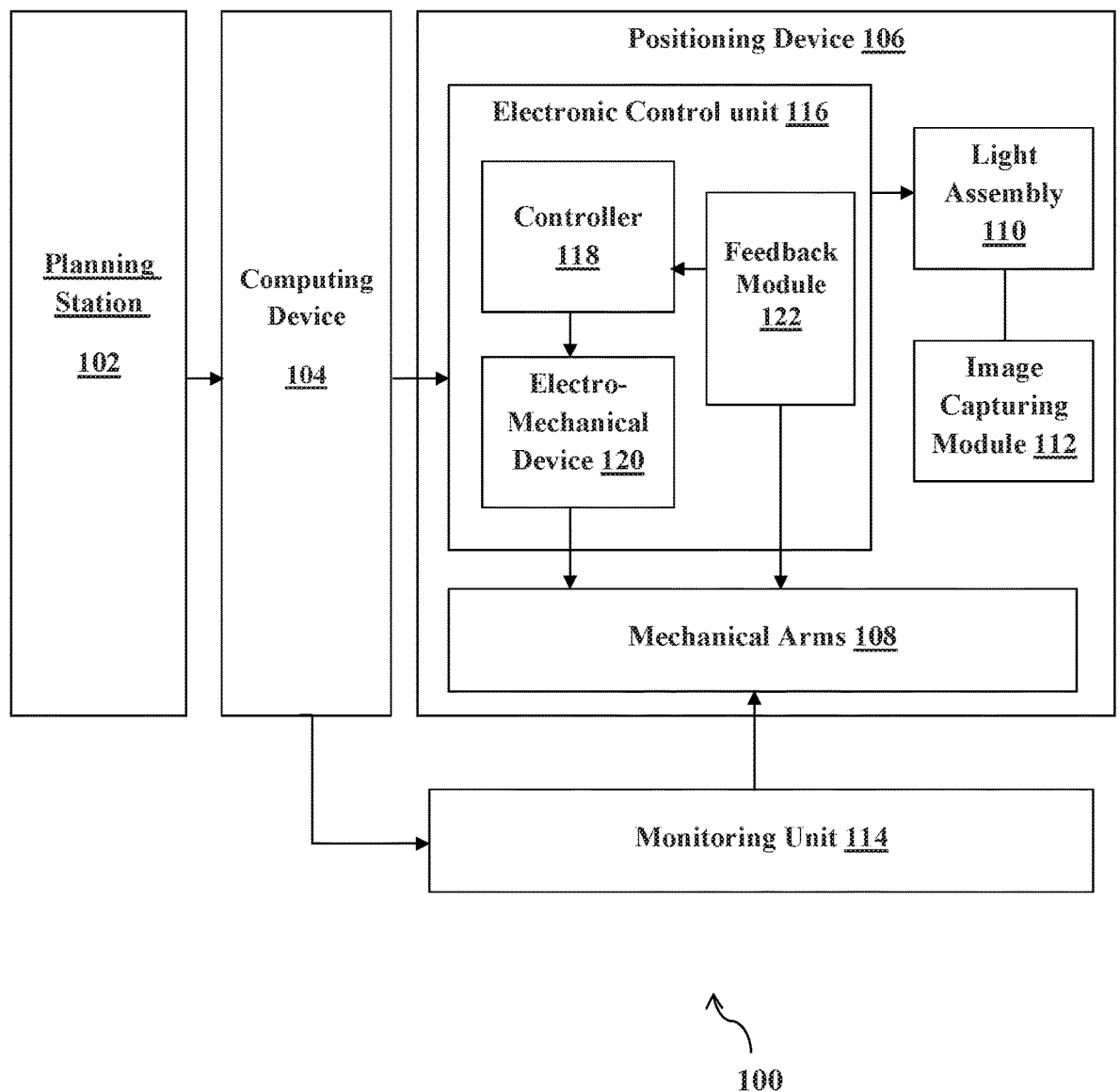
FIG. 1 illustrates a functional block diagram of a light and shadow guided needle positioning system, according to one embodiment of the present invention.

Although the specific features of the present invention are shown in some drawings and not in others. This is done for convenience only as each feature may be combined with any or all of the other features in accordance with the present invention.

DETAILED DESCRIPTION OF THE INVENTION

In the following detailed description, reference is made to the accompanying drawings that form a part hereof, and in which the specific embodiments that may be practiced is shown by way of illustration. These embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments of the present invention provide a system for positioning a needle based on light and shadow. The system comprises a planning station for receiving and displaying a Digital Imaging and Communications in Medicine (DICOM) images of a patient from an imaging device in order to select a point of insertion of a needle on the patient's body and a target point inside the patient's body. A computing device is configured for computing the needle coordinates based on the captured images and selected point of insertion and target point. The needle coordinates comprise two angles of insertion and insertion length of the needle to reach the target point. The computing device is also configured to display a virtual needle path based on the DICOM images before actual insertion as a precautionary safety measure. The computed angle is an orbital angle and a crano-caudal angle. A positioning device is configured for positioning one or more mechanical arms based on the computed needle coordinates. The positioning devices is configured to move in horizontal direction on X axis, vertical direction on Y axis manually and the one or more mechanical arms in the positioning device are configured to move in horizontal direction on X axis, vertical direction on Y axis, orbital angle on A axis and crano-caudal angle on Z axis. In one embodiment, the positioning device can be fixed at the ceiling or at the pillar and trailing arrangement in the medical procedure room. The positioning device can be moved horizontally in X axis and vertically in Y axis towards the patient automatically. A light assembly is provided in the positioning device and is configured for projecting light at a particular angle on the needle placed at the point of insertion to form shadows of the needle using one or more LED lights. The light assembly is further includes a laser source which projects a cross hair at the point of insertion. An image capturing module is provided in the positioning device and is configured for continuously capturing images or video of the point of insertion, shadow of the needle and the cross hair. A centre of the image capturing module is aligned with the point of insertion marked on the patient's body. A monitoring unit is configured for displaying images or video captured using image capturing module. The monitoring unit is configured for projecting a virtual circle on the displayed images or video and for monitoring the alignment of the virtual circle with the point of insertion, shadow of the needle and the cross hair in order to facilitate precise insertion of the needle.

According to one embodiment of the present invention, the positioning device comprises an electronic control unit configured to receive the needle coordinates from the computing device and transform the needle coordinates into orbital and crano-caudal movement of the one or more mechanical arms in the positioning device.

According to one embodiment of the present invention, the electronic control unit comprises a controller configured for processing the received needle coordinates to generate corresponding electric signal. The electronic unit also comprises but not limited to an electromechanical device. The electromechanical device is configured to move the positioning device in horizontal direction on X axis, vertical direction on Y axis and the one or more mechanical arms in orbital angle on A axis and crano-caudal angle on Z axis based on the electric control signal/command received from the controller. The electronic control unit further comprises a feedback module configured for monitoring the movement of the one or more mechanical arms in A-axis and Z axis for deviation from the computed needle coordinates. The feedback module is configured for providing a feedback to the controller about the deviations for enabling corrective action.

According to one embodiment of the present invention, the LED lights within the light assembly are configured based on one or more parameters such as a number of lights, angle of light, tilt angle and light intensity to generate different shadow patterns and shadow lengths of the needle.

According to one embodiment of the present invention, the laser lights within the light assembly are configured based on one or more parameters such as a number of beams, angle of beam, tilt angle and beam intensity to generate different cross hair patterns at the point of insertion.

According to one embodiment of the present invention, a method is provided for precise positioning of a needle using a light and shadow. The method involves receiving and displaying plurality of DICOM images, selecting a point of insertion of the needle on the patient's body and a target point inside the patient's body, computing needle coordinates and assist in aligning the needle using combination of shadow of the needle and laser cross-hair.

According to one embodiment of the present invention, the method comprising the steps of receiving and displaying plurality of DICOM images of a patient for selecting a point of insertion of a needle on the patient's body and a target point inside the patient's body. The needle coordinates are calculated based on the captured images. The needle coordinates comprise two angles of insertion and length of the needle insertion to reach the target point. The computed angle is an orbital angle and a cranocaudal angle. One or more mechanical arms are positioned based on the computed needle coordinates. The positioning device is configured to move in horizontal direction on X axis, vertical direction on Y axis, one or more mechanical arms are configured to move in orbital angle on A-axis and crano-caudal angle on Z axis. An illuminating light beam is projected at a particular angle on the needle placed at the point of insertion to form shadows of the needle using one or more LED lights. A laser light beam is projected to form a cross hair at the point of insertion. The images or a video of the point of insertion, shadows of the needle and the cross hair are continuously captured using an image capturing module. A centre or focus of the image capturing module is aligned with the point of insertion marked on the patient's body. The images or video captured using image capturing module is displayed on a monitoring unit. The monitoring unit is configured for projecting a virtual circle on the displayed images or video and for monitoring the alignment of the virtual circle with the point of insertion, shadow of the needle and the cross hair in order to facilitate a precise insertion of the needle.

According to one embodiment herein, scanogram and axial section of the patient is taken and the point of insertion and the target point inside the patient's body is marked using CT console/table by the clinician manually. The point of insertion is measured from patient midline on the image and is marked with radio opaque fiducially. The DICOM images of the point of insertion are taken and forwarded to the computing device. The point of insertion and target point are registered on the computing device. Further, the computing device is configured to calculate the needle coordinates. The needle coordinates are then passed on to the positioning device to tilt the one or more mechanical arms by adjusting the movement along A-axis and Z axis, when needed. The centre of the image capturing module is aligned to the point of insertion to see the real time feed from the image capturing module. The one or more LED lights and laser lights are placed right angle to each other to form shadows of the needle and cross hair. Additional reference points are drawn on patient's body to detect any patient movement. A virtual circle is projected on the monitoring unit. The shadows of the needle, cross hair and virtual circle are aligned with the point of insertion. The stopper is marked at the needle based on the length of insertion computed at the computing device. Finally, needle is inserted through the point of insertion till the stopper marked at the needle in order to reach target location and by aligning the shadows with the laser cross-hair.

FIG. 1 illustrates a functional block diagram of a light and shadow guided needle positioning system, according to one embodiment of the present invention. The system comprises a planning station 102, a computing device 104 and a positioning device 106. The positioning device 106 comprises one or more mechanical arms 108, a light assembly 110, an image capturing module 112, a monitoring unit 114 and an electronic control unit 116. The electronic control unit 116 is provided with a controller 118, an electromechanical device 120 and a feedback module 122.

According to an embodiment herein, the planning station 102 is provided. The planning station 102 is configured to receive and display plurality of DICOM images of a patient in order to select a point of insertion of a needle on the patient body and a target point inside the patient's body. The point of insertion and the target point are selected by a clinician on referring the DICOM images received at the planning station 102.

According to an embodiment herein, the computing device 104 is connected to the planning station 102 and is configured to compute needle coordinates based on the point of insertion and target point selected at the planning station 102. The needle coordinates comprise two angles of insertion and length of the needle to reach the target point. The computed angle of insertion is an orbital angle and a crano-caudal angle. The computing device 104 also provides additional information to the clinician by displaying a virtual needle path based on captured DICOM images before actual needle insertion as a precautionary safety measure.

According to an embodiment herein, the positioning device 106 is connected with the computing device 104 and is configured for positioning one or more mechanical arms 108 as per the computed needle coordinates. The one or more mechanical arms 108 are configured to move in, orbital angle on A-axis and crano-caudal angle on Z axis. The positioning device 106 also comprises the electronic control unit 116 configured to receive the needle coordinates from the computing device 104 and transform the needle coordinates into orbital and crano-caudal movement of the one or more mechanical arms 108.

The electronic control unit 116 is provided with a controller 118 configured for processing the received needle coordinates to generate corresponding electric signal. The electronic control unit 116 comprises the electromechanical device 120 configured for moving the one or more mechanical arms 108 in orbital angle on A-axis and cranocaudal angle on Z axis based on the electric signal/command received from the controller 118. The electronic control unit 116 comprises a feedback module 122 configured for monitoring the movement of the one or more mechanical arms 108 in A axis and Z axis for any deviation from the computed needle coordinates. The feedback module 122 is configured for providing a feedback to the controller 118 regarding the deviations for initiating a corrective action.

According to an embodiment herein, the system comprises a light assembly 110 configured to shed light at a particular angle on the needle placed at the point of insertion to form shadows of the needle using one or more LED lights. The light assembly 108 is further configured to project laser light beams to form a cross hair at the point of insertion.

According to one embodiment herein, the LED lights within the light assembly 110 are configured based on one or more parameters such as number of lights, angle of light, tilt angle and light intensity to generate different shadow patterns and shadow lengths of the needle. Further, the laser light beams within the light assembly 110 are configured based on one or more parameters such as number of beams, angle of beam, tilt angle and beam intensity to generate different cross hair patterns at the point of insertion.

According to an embodiment herein, the image capturing module 112 is configured for continuously capturing the images or video of the point of insertion, shadow of the needle and the cross-hair. A centre of the image capturing module 112 is aligned with the point of insertion marked on the patient's body.

According to an embodiment herein, the monitoring unit 114 is configured for displaying the images or video captured using the image capturing module 112. The monitoring unit 114 is configured for projecting a virtual circle on the displayed images or video and for monitoring the alignment of the virtual circle with the point of insertion, shadow of the needle and the cross-hair in order to facilitate precise insertion of the needle.

According to an embodiment herein, the one or more mechanical arms 108 are calibrated based on the computed needle coordinates to enable a clinician is to move the one or more mechanical arms 108 and the patient table to a desired position with the help of image capturing module 112. The one or more mechanical arms 108 are moved to coincide with the centre of the image capturing module 112 (visualized through the centre point of the image capturing module 112) to align with the point of insertion marked on the patient's body. The clinician places the needle and orients the needle in such a way that the centre of the needle (needle tip) aligns with the centre of the image capturing module 112. The one or more LED lights from the light assembly 110 are configured or designed to project the light beams at particular angles. According to an embodiment herein, at least two lights arranged at mutually perpendicular positions (at 90-degree to each other) to project the light on the needle to form shadows. A number of shadows are formed based on the number of lights used. The clinician puts stopper at the needle based on the insertion length computed at the computing device and the clinician aligns the shadows to coincide with the needle coordinates to reassure that the top of the needle is positioned at the exact centre of the image. The needle is then pushed in by continuously monitoring until the needle is inserted into the body until the stopper along a predicted/estimated path by superimposing the shadows on the laser cross hair.

According to an embodiment herein, the clinician draws reference points on the patient's body and registers the points on the monitoring unit 114 which in turn is aligned exactly to the centre of the image capturing module 112, after aligning the one or more mechanical arms 108 with the centre of the image capturing module 112. The image capturing module 112 continuously captures the images of the reference points in real time and sends them to the computing device 104. The reference points get moved when the patient moves his/her body. Information of the patient movement is determined at the computing device 104 by continuously comparing the position of reference points at the one or more images captured by the image processing module 112 at real time. The computing device 104 alerts the clinician through the monitoring unit 114 if any movement of the reference points is detected. In another embodiment, the computing device 104 also detects the distance and direction of the movement of reference points. Further, the computing device 104 sends signal to move a support (example CT couch 204) where the patient body is laid, in order to compensate the distance and direction detected at computing device 104. The patient is asked to control the breath so that the cross hair on the patient's body is aligned to centre of the image capturing module 112 thereby improving an accuracy of prediction/estimation. Based on the movement of the patient, the clinician is enabled to re-plan the procedure in case of any need or requirement. It is important to have the breath hold of patient at same level when the DICOM images are taken as well as while positioning the needle and thus eliminates the erroneous point of needle entry at the patient's body due to inconsistent breath hold. In this embodiment, the clinician can instruct the patient to maintain the consistent breath hold with the help of the monitoring unit 114 and image capturing module 112. In one embodiment, the monitoring unit 114 includes a touch screen display and it is configured to receive one or more markings. The one or more markings are drawn by covering either the shadows of the needle and/or the virtual circle which are displayed therein. In case the patient is moved away from bed and then the patient can be bring back to the position by tracing the shadows of the needle and virtual circle exactly to the markings at the monitoring unit.

According to one embodiment herein, scanogram and axial section of the patient is taken and the point of insertion and the target point inside the patient's body is marked using CT console/table by the clinician manually. The point of insertion is measured from patient midline on the image and is marked with radio opaque fiducially. The DICOM images of the point of insertion are taken and forwarded to the computing device 104. The point of insertion and target point are registered on the computing device 104. Further, the computing device 104 is configured to calculate the needle coordinates. The needle coordinates are then passed on to the positioning device 106 to tilt the one or more mechanical arms 108 by adjusting movement in A-axis and Z axis when needed. The centre of the image capturing module 112 is aligned to the point of insertion to see the real time feed from the image capturing module 112. The one or more LED lights and laser lights which are placed right angle to each other forming shadow of the needle and cross hair are switched on. Additional reference points are drawn on patient's body to detect any patient movement. A virtual circle is projected on the monitoring unit 114. The shadows of the needle, cross hair and virtual circle are aligned with the point of insertion. The stopper is marked at the needle based on the length of insertion computed at the computing device 104. Finally, needle is inserted through the point of insertion till the stopper marked at the needle in order to reach target location and by aligning the shadows with the laser cross-hair.

Figure 2:
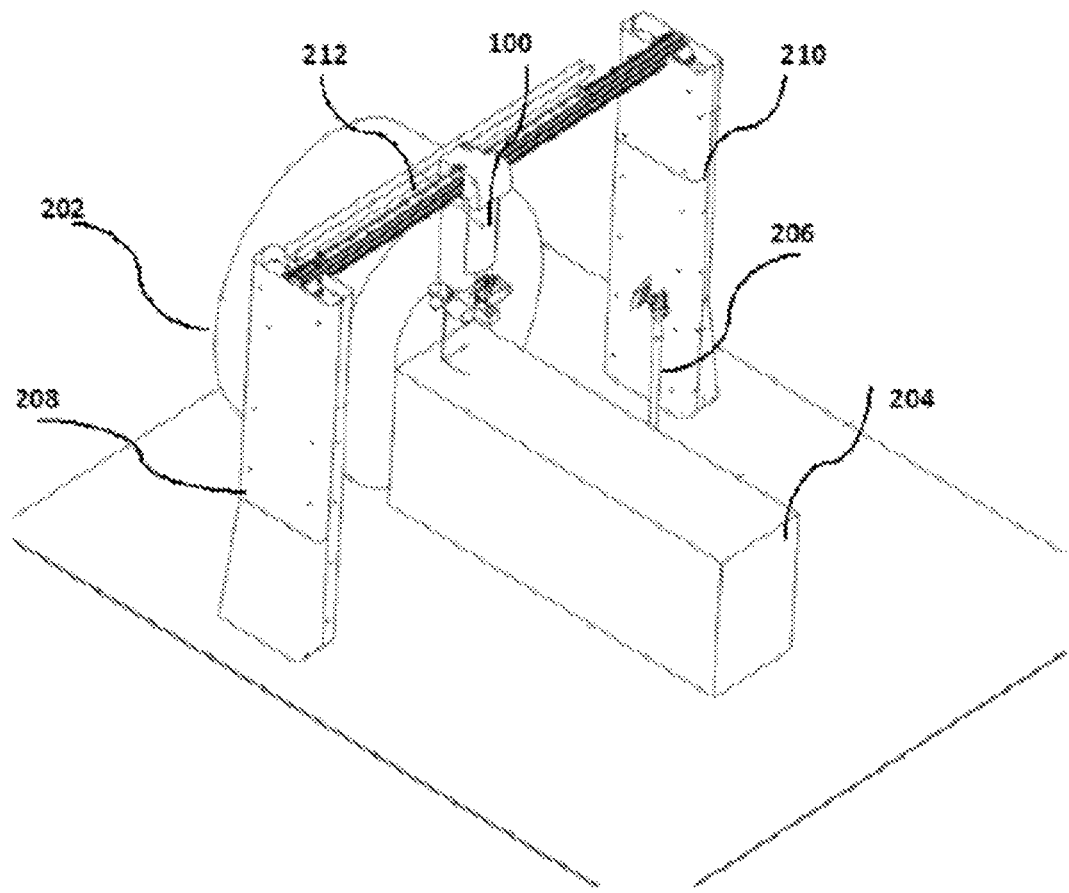
FIG. 2 illustrates a perspective view of a light and shadow guided needle positioning system assembled with a CT scan machine, according to one embodiment of the present invention.

FIG. 2 illustrates a perspective view of a light and shadow guided needle positioning system assembled with a CT scan machine, according to one embodiment of the present invention. With respect to FIG. 2, the assembly comprises a CT gantry 202, a CT couch 204, a light and shadow guided needle positioning system 100, a monitor stand 206, left pillar 208 and a right pillar 210. The left pillar 208 and the right pillar 210 are configured to attach the light and shadow guided needle positioning system 100 with the CT scan machine. According to one embodiment herein, the positioning device 106 is mounted on a mechanical rail 212 perpendicular to the patient table.

Figure 3:
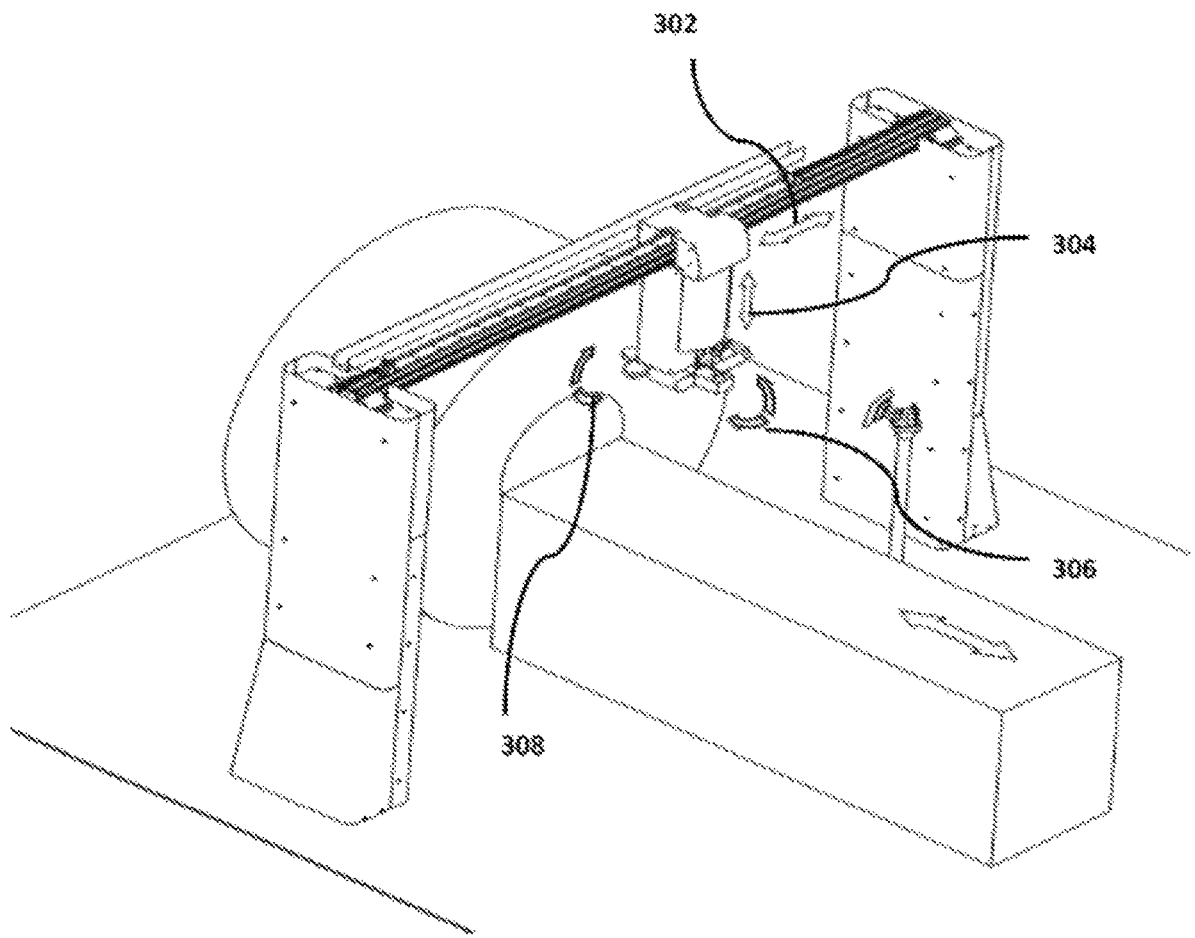
FIG. 3 illustrates a perspective view of a light and shadow guided needle positioning system assembled with a CT scan machine and indicating an axial movement, according to one embodiment of the present invention.

FIG. 3 illustrates a perspective view of a light and shadow guided needle positioning system assembled with a CT scan machine and indicating an axial movement, according to one embodiment of the present invention. With respect to FIG. 3, the movement of the positioning device 106 is shown in horizontal direction on X axis (302), vertical direction on Y axis (304), orbital angle on A-axis (306) and crano-caudal angle on Z axis (308). According to one embodiment herein, the X axis is moved parallel to the plane of the CT scan machine and is driven by a motor. Any desired movement across the plane in X axis is carried out by the press operation of a switch. The Y axis is moved up and down and configured to position the positioning device 106 as closer to the patient's body. Y axis movement is controlled by a geared motor. The orbital and crano caudal angle is controlled by geared motor. The movement is controlled automatically based on the inputs from the computing device 104. The motor can be stepper motor or servo motor or any other motor used to perform the defined functionality.

Figure 4:
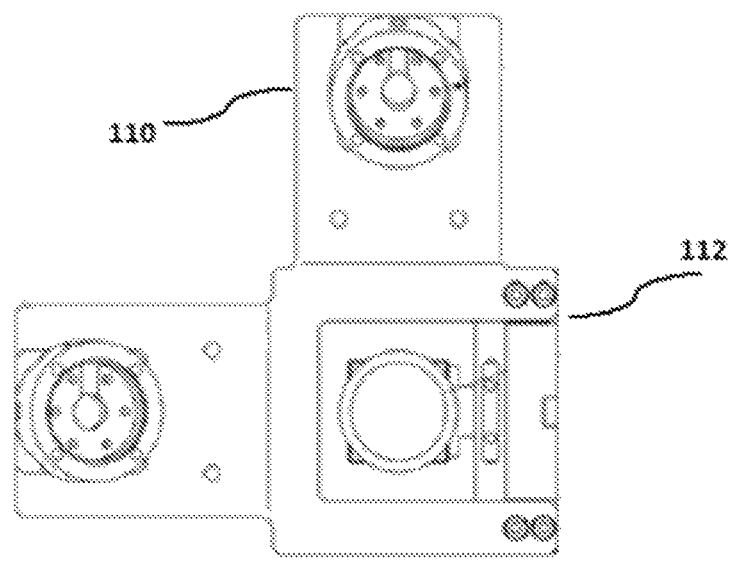
FIG. 4 illustrates a bottom view of a light assembly and an image capturing module in a light and shadow guided needle positioning system, according to one embodiment of the present invention.
Figure 5:
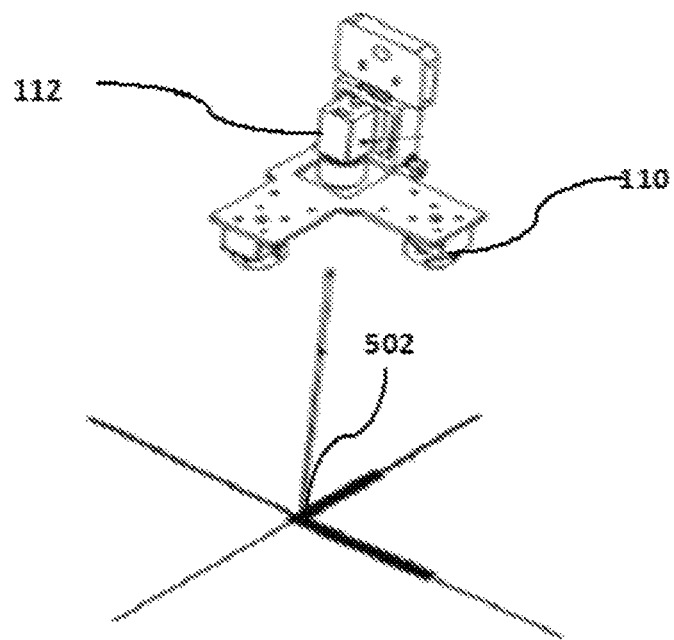
FIG. 5 illustrates a side perspective view of a light assembly and an image capturing module in a light and shadow guided needle positioning system, according to one embodiment of the present invention.

FIG. 4 illustrates a bottom view of a light assembly and an image capturing module in a light and shadow guided needle positioning system, according to one embodiment of the present invention. FIG. 5 illustrates a side perspective view of a light assembly and an image capturing module in a light and shadow guided needle positioning system, according to one embodiment of the present invention. With respect to FIG. 4 & FIG. 5 the light assembly 110 and the image capturing module 112 are engineered in such a way that the centre of the image capturing module 112 is always positioned in the exact centre of the positioning device 106. The one or more LED light beams from the light assembly 110 are projected exactly at the estimated angles from the centre of the positioning device 106. The top of needle 502 is positioned at the center of the shadows of the needle and the cross-hair image is formed using laser light beams.

Figure 6:
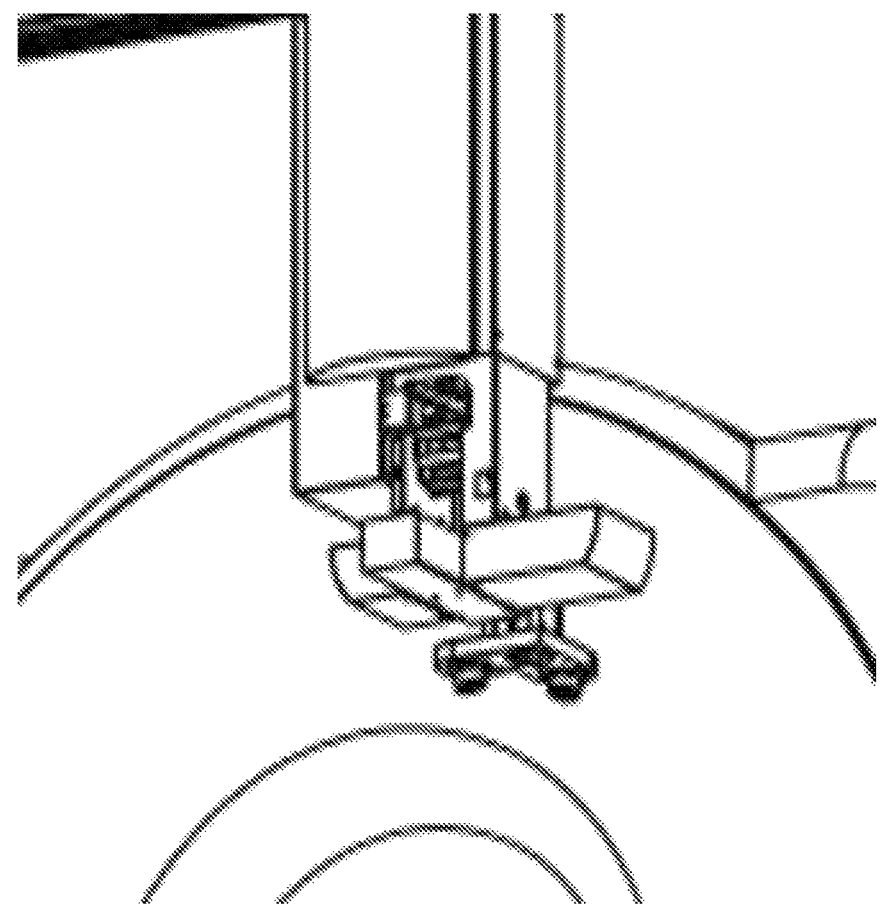
FIG. 6 illustrates a photographic image of the light and shadow guided needle positioning system assembled with a CT scan machine, according to one embodiment of the present invention.

FIG. 6 illustrates a photographic image of the light and shadow guided needle positioning system assembled with a CT scan machine, according to one embodiment of the present invention. With respect to FIG. 6, the various components of the light and shadow guided needle positioning system are observed from the image.

Figure 7:
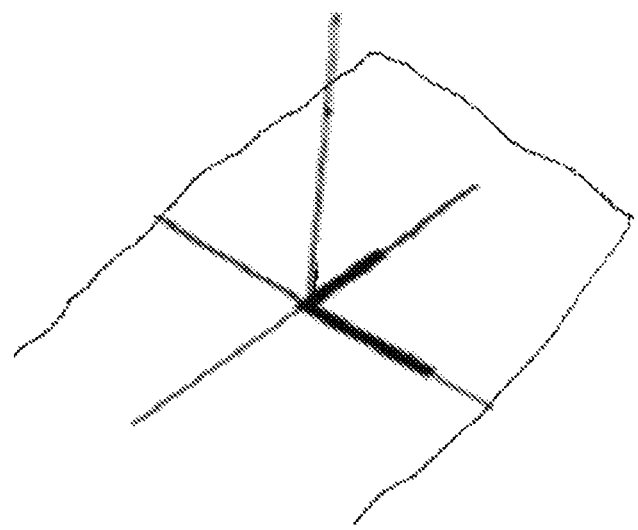
FIG. 7 illustrates an image of the top of the needle placed exactly on the centre of the cross hair formed using laser lights and the shadows of the needle aligned to the limbs of the cross hair in a light and shadow guided needle positioning system, according to one embodiment of the present invention.

FIG. 7 illustrates an image of the top of the needle placed exactly on the centre of the cross hair formed using laser lights and the shadows of the needle aligned to the limbs of the cross hair in a light and shadow guided needle positioning system, according to one embodiment of the present invention. With respect to FIG. 7 an image of the top of the needle is placed exactly on the centre of the cross hair formed using laser lights and the shadows of the needle aligned to the limbs of the cross hair, according to one embodiment of the present invention. This alignment of the shadows of the needle with the cross hair is very important to ensure precise point of insertion.

Figure 8:
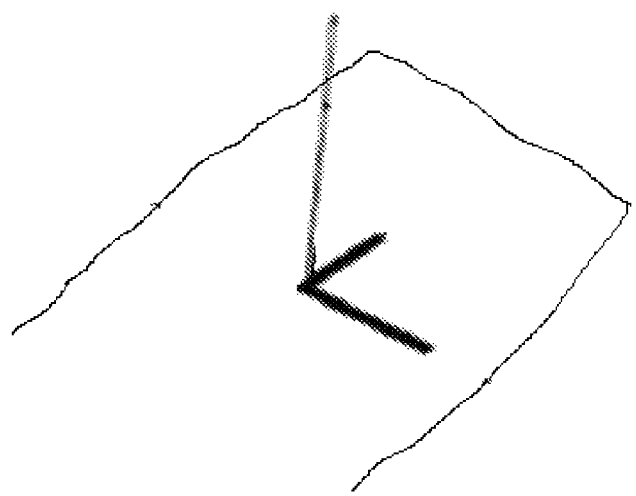
FIG. 8 illustrates an image of a needle with shadows after the laser lights are switched off in a light and shadow guided needle positioning system, according to one embodiment of the present invention.

FIG. 8 illustrates an image of a needle with shadows after the laser lights are switched off in a light and shadow guided needle positioning system, according to one embodiment of the present invention. With respect to FIG. 8, the one or more LED lights are tilted for getting lengthier shadows and the intensity of the lights is also adjusted or switched off or strobed as desired by the clinician for a proper viewing of the shadows.

Figure 9:
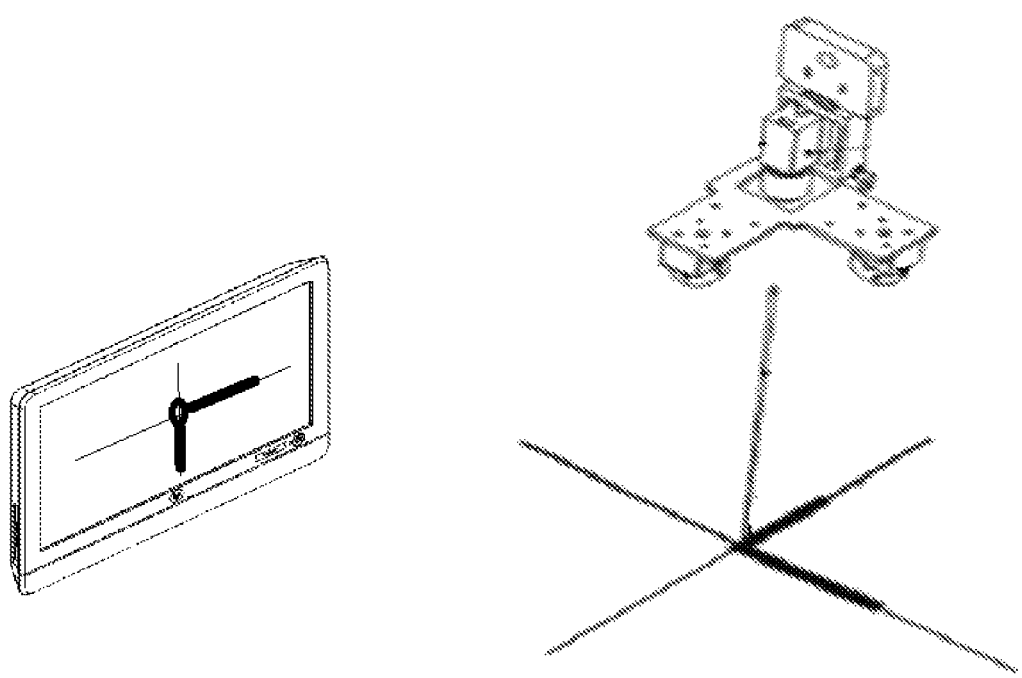
FIG. 9 illustrates an image of a monitoring unit displaying needle with shadows perfectly aligned to the cross hair formed using laser lights in a light and shadow guided needle positioning system, according to one embodiment of the present invention.

FIG. 9 illustrates an image of a monitoring unit displaying needle with shadows perfectly aligned to the cross hair formed using laser lights in a light and shadow guided needle positioning system, according to one embodiment of the present invention. With respect to FIG. 9, the top of the needle is positioned exactly in the centre of the virtual circle projected at the centre of the point of insertion.

Figure 10:
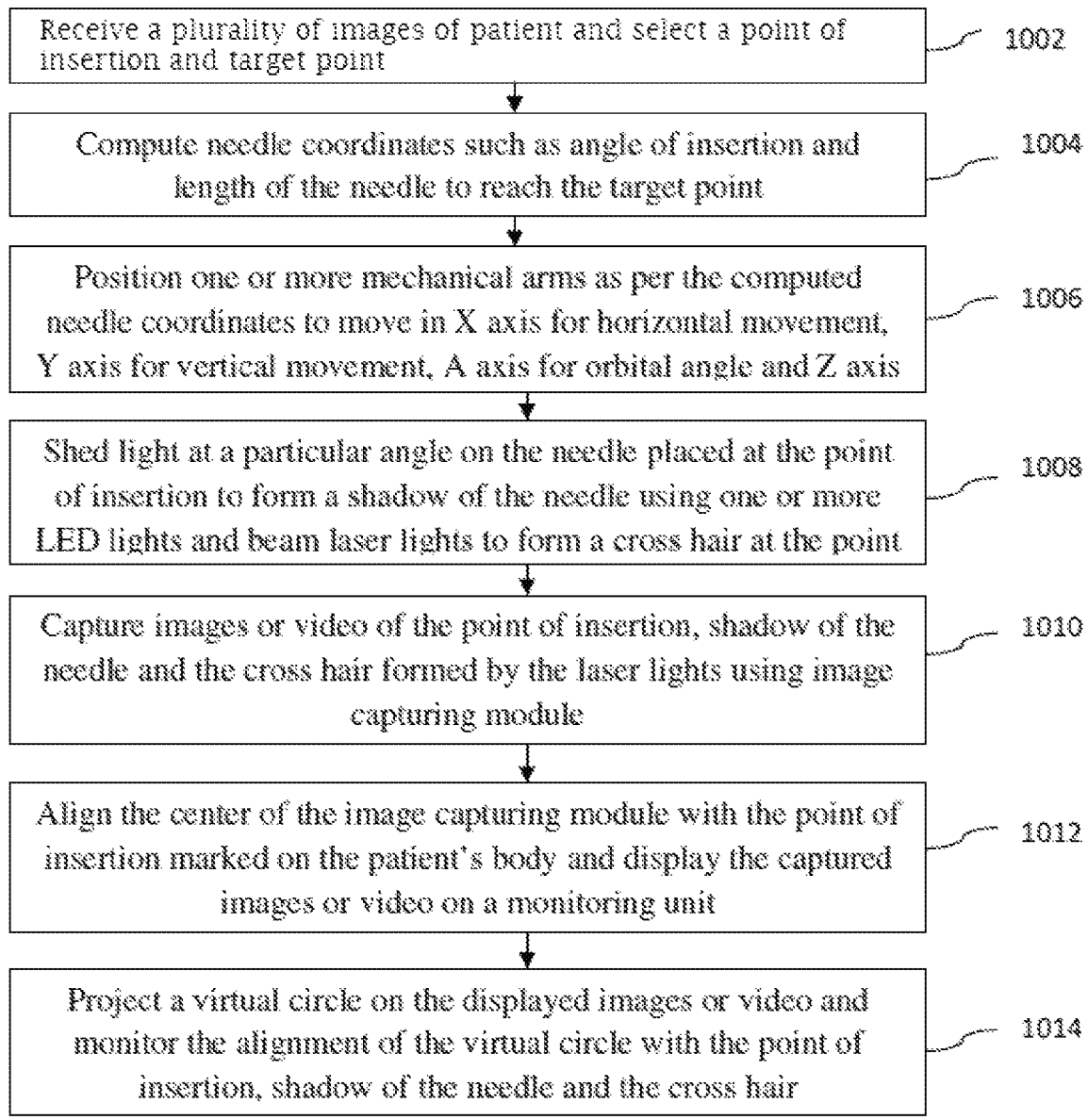
FIG. 10 illustrates a flow chart explaining a method for precise positioning of a needle with a light and shadow guided needle positioning system, according to an embodiment of the present invention.

FIG. 10 illustrates a flow chart explaining a method for precise positioning of a needle with a light and shadow guided needle positioning system, according to an embodiment of the present invention. With respect to FIG. 10, a method is provided for precise positioning of a needle by capturing plurality of DICOM images, identifying a point of insertion of the needle on the patient's body and a target point inside the patient's body, computing needle coordinates and aligning the needle using shadow of the needle and light through visual analysis is provided. The DICOM images of a patient are captured for identifying a point of insertion of a needle on the patient's body and a target point inside the patient's body (1002). The needle coordinates are computed based on the captured images (1004). The needle coordinates comprise two angles of insertion and length of the needle insertion to reach the target point. The computed angle is an orbital angle and a crano-caudal angle. One of more mechanical arms are positioned based on the computed needle coordinates (1006). The one or more mechanical arms are configured to move in horizontal direction on X axis, vertical direction on Y axis, orbital angle on A-axis and crano-caudal angle on Z axis. A Light beam is projected at a particular angle on the needle placed at the point of insertion to form shadows of the needle. One or more LED lights and laser lights are projected to form a cross-hair at the point of insertion (1008). Images or video of the point of insertion, shadow of the needle and the cross hair are continuously captured using an image capturing module (1010). A centre of the image capturing module is aligned with the point of insertion marked on the patient's body and the captured images or video with an image capturing module are displayed on a monitoring unit (1012). The monitoring unit is configured for projecting a virtual circle on the displayed images or video and for monitoring the alignment of the virtual circle with the point of insertion, shadow of the needle and the cross hair in order to facilitate precise insertion of the needle (1014).

According to one embodiment herein, a method is provided for calculating the needle coordinates and positioning the needle using shadow of the needle and lights. The method is implemented in conjunction with a CT scan machine. According to one embodiment herein, scanogram and axial section of the patient is taken and the point of insertion and the target point inside the patient's body is marked using CT console/table by the clinician manually. The point of insertion is measured from patient midline on the image and is marked with radio opaque fiducially. The DICOM images of the point of insertion are taken and forwarded to the computing device. The point of insertion and target point are registered on the computing device. Further, the computing device is configured to calculate the needle coordinates. The needle coordinates are then passed on to the positioning device to tilt the one or more mechanical arms by adjusting the movement along A axis and Z axis, when needed. The centre of the image capturing module is aligned to the point of insertion to see the real time feed from the image capturing module. The one or more LED lights and laser lights are placed right angle to each other to form shadows of the needle and cross hair. Additional reference points are drawn on patient's body to detect any patient movement. A virtual circle is projected on the monitoring unit. The shadows of the needle, cross hair and virtual circle are aligned with the point of insertion. Finally, needle is inserted through the point of insertion till the stopper marked at the needle in order to reach target location and by aligning the shadows with the laser cross-hair.

The foregoing description of the specific embodiments will so fully reveal the general nature of the present invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the present invention have been described in terms of preferred embodiments, those skilled in the art will recognize that the present invention can be practiced with modification within the spirit and scope of the appended claims.

The various embodiments of the present invention provide a system and method for light and shadow guided needle positioning which accurately positions the needle towards a point of insertion on a patient's body without making any direct contact with the patient's body. The system and method of the present invention requires only one time calibration even for repeated usage. Further, the system and method of the present invention promptly identifies any needle erroneous tilting via continuous shadow monitoring of the needle. Further, as the system of the invention does not come in physical contact with the patient and stands well away from the patient's body sterilization of the system is not required. The system and method for guiding the Needle is used for and not limited to biopsy, liquid aspiration, multiple-needle insertion, targeted tumor ablation, etc.

Although the embodiments herein are described with various specific embodiments, it will be obvious for a person skilled in the art to practice the invention with modifications. However, all such modifications are deemed to be within the scope It is also to be understood that the following claims are intended to cover all of the generic and specific features of the embodiments described herein and all the statements of the scope of the embodiments which as a matter of language might be said to fall there between.

The invention claimed is:

1. A light and shadow guided needle positioning system comprising a positioning device, a light assembly, an image capturing module, and a monitoring unit, the system being configured for:
   receiving a plurality of images of a patient from an imaging device and for selecting a point of insertion of a needle on the patient's body and a target point inside the patient's body;
   computing needle coordinates based on the point of insertion and target point, and wherein the needle coordinates comprise two angles of insertion and a length of the needle insertion to reach the target point, wherein the two angles comprise an orbital angle and a crano-caudal angle;
   positioning, by the positioning device, one or more mechanical arms based on the computed needle coordinates, and wherein the positioning device is adapted to move in a horizontal direction along an X axis, a vertical direction along a Y axis, and the mechanical arms are adapted to move in the orbital angle along an A axis and in the crano-caudal angle along a Z axis;
   projecting, by the light assembly, light beams at a preset angle on the needle placed at the point of insertion to form shadows of the needle, and wherein the light assembly is adapted to project the light beams to form a cross hair at the point of insertion;
   continuously capturing, by the image capturing module, images or video of an area of interest comprising (i) the point of insertion, (ii) shadows of the needle and (iii) the cross hair, and wherein a centre of the image capturing module is aligned with the point of insertion marked on the patient's body; and
   displaying, by the monitoring unit, the images or video captured with the image capturing module, and wherein the monitoring unit is configured for projecting a virtual circle on the displayed images or video and for monitoring the alignment of the virtual circle with the point of insertion, and the shadows of the needle with the cross hair to facilitate insertion of the needle.

2. The system of claim 1, wherein the light assembly comprises one or more Light Emitting Diode (LED) lights and a laser light source, and wherein the light assembly is adapted to project laser light beams to form the cross hair at the point of insertion and to cast shadows of the needle aligned to the cross hair when the needle is interested in the planned angle.

3. The system of claim 2, wherein the LED lights within the light assembly are adapted based one or more parameters selected from a group consisting of a number of lights, angle of light, tilt angle and light intensity to generate a plurality of shadow patterns and shadow lengths of the needle, and wherein the plurality of shadow patterns are mutually different shadow patterns.

4. The system of claim 2, wherein the laser light source within the light assembly is adapted based on one or more parameters selected from a group consisting of a number of beams, angle of beam, tilt angle and beam intensity to generate a plurality of cross hair patterns at the point of insertion, and wherein the plurality of cross-hair patterns are mutually different cross-hair patterns.

5. The system of claim 1, wherein the computing device is adapted to display a virtual needle path based on the plurality of images before an actual needle insertion as a precautionary safety measure.

6. The system of claim 1, wherein the positioning device comprises an electronic control unit adapted to receive the needle coordinates from the computing device to generate commands for moving the one or more mechanical arms along orbital axes and crano-caudal angles.

7. The system of claim 6, wherein the electronic control unit comprises:
   a controller for processing the received needle coordinates to generate corresponding command signal or electric signal;
   an electromechanical device adapted to move the positioning device in the horizontal direction on the X axis, the vertical direction on the Y axis and the one or more mechanical arms in the orbital angle on the A axis and the crano-caudal angle on the Z axis based on the electric signal or command received from the controller; and
   wherein the system is further configured for monitoring the movement of the positioning device along the X axis, the Y axis, the A axis and the one or more mechanical arms along the Z axis for any deviation from the computed needle coordinates.

8. A method for positioning a needle comprising steps of:
   receiving a plurality images of a patient for selecting a point of insertion of a needle on the patient's body and a target point inside the patient's body;
   calculating, by a computing device, needle coordinates based on the point of insertion and the target point selected at the planning station, and wherein the needle coordinates comprise two angles of insertion and length of the needle insertion required to reach the target point, and wherein the computed angle is an orbital angle and a crano-caudal angle;
   positioning, by a positioning device, one or more mechanical arms based on the computed needle coordinates;
   moving the position device in horizontal direction along X axis, vertical direction along Y axis and the one or more mechanical arms are adapted to move in the orbital angle along A axis and in the crano-caudal angle along Z axis;
   projecting, by a lighting assembly, light beam from one or more LED lights at a preset angle on the needle placed at the point of insertion to form shadows of the needle and projecting a laser light beam to form a cross hair at the point of insertion;
   continuously, by an image capturing module, capturing images or video of the point of insertion, shadow of the needle and the cross hair, and wherein a centre of the image capturing module is aligned with the point of insertion marked on the patient's body; and
   displaying images or video captured with the image capturing module on a monitoring unit, and wherein the monitoring unit is configured for projecting a virtual circle on the displayed images or video and for monitoring the alignment of the virtual circle with the point of insertion, shadow of the needle and the cross hair in order to facilitate precise insertion of the needle,
   inserting the needle in the patient's body at center of the cross-hair by (i) aligning the needle tip at the cross hair centre, (ii) aligning the shadows of needle to the cross-hairs and (ii) aligning a head of the needle with the virtual circle displayed at the monitoring unit.

9. The method of claim 8, wherein positioning one or more mechanical arms based on the computed needle coordinates comprises:
   processing, by a controller, the needle coordinates received at positioning device to generate corresponding command signal or electric signal;

moving, by an electromechanical device, the positioning device in the horizontal direction on the X axis, the vertical direction on the Y axis and the one or more mechanical arms in the orbital angle on the A axis and the crano-caudal angle on the Z axis based on the electric signal or command received from the controller; and monitoring the movement of the positioning device along the X axis, the Y axis and the one or more mechanical arm along the A axis and the Z axis for any deviation from the computed needle coordinates.

\* \* \* \* \*